United States Patent
Lurvey et al.

(10) Patent No.: US 8,679,075 B2
(45) Date of Patent: Mar. 25, 2014

(54) INFUSION DELIVERY SYSTEM

(75) Inventors: Kent Lurvey, Grayslake, IL (US); Alan Brundle, West Bergholt (GB); Troy Wert, Spring Grove, IL (US); Peter Bojan, Grayslake, IL (US); John Darvasi, Hawthorne Woods, IL (US); Peter Tomicki, Janesville, WI (US); Craig Sandford, Buffalo Grove, IL (US); Thomas McGraghan, Libertyville, IL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 1700 days.

(21) Appl. No.: 11/345,512

(22) Filed: Jan. 31, 2006

(65) Prior Publication Data

US 2006/0224128 A1    Oct. 5, 2006

Related U.S. Application Data

(60) Provisional application No. 60/649,396, filed on Feb. 1, 2005.

(51) Int. Cl.
*A61M 5/00*    (2006.01)

(52) U.S. Cl.
USPC .......................................... 604/250; 604/65

(58) Field of Classification Search
USPC .......... 604/250, 65–67, 131, 33, 34, 246, 249
See application file for complete search history.

(56) References Cited

U.S. PATENT DOCUMENTS

| | | | |
|---|---|---|---|
| 4,687,942 A * | 8/1987 | Takagi et al. ................. 250/556 |
| 5,290,239 A | 3/1994 | Classey et al. |
| 5,300,044 A * | 4/1994 | Classey et al. ................. 604/250 |
| 5,378,231 A * | 1/1995 | Johnson et al. ................. 604/67 |
| 5,393,967 A * | 2/1995 | Rice et al. ..................... 235/454 |
| 5,842,841 A | 12/1998 | Danby et al. |
| 6,117,115 A * | 9/2000 | Hill et al. ....................... 604/250 |
| 6,123,524 A | 9/2000 | Danby et al. |
| 6,600,418 B2 | 7/2003 | Francis et al. |
| 6,635,033 B1 | 10/2003 | Hill et al. |
| 7,927,313 B2 * | 4/2011 | Stewart et al. ................. 604/189 |
| 2004/0104271 A1 | 6/2004 | Martucci et al. |
| 2005/0277873 A1 | 12/2005 | Stewart et al. |

FOREIGN PATENT DOCUMENTS

| | | |
|---|---|---|
| WO | WO 00/21431 | 4/2000 |
| WO | WO 03/030962 | 4/2003 |

OTHER PUBLICATIONS

International Search Report for International Application No. PCT/US 06/03499 of Applicant Baxter International Inc.
Canadian Office Action for Application No. 2,596,259 mailed Apr. 20, 2012.
Mexican Office Action issued Mar. 14, 2013 for related Mexican Appln. No. MX/a/2007/009289.

* cited by examiner

*Primary Examiner* — Kevin C Sirmons
*Assistant Examiner* — Phillip Gray
(74) *Attorney, Agent, or Firm* — K&L Gates LLP

(57) ABSTRACT

A system and method for automatically delivering an infusate to a patient is disclosed. The system includes an infusion set and an infusion device. A signaling component disposed on an infusion set component identifies an administration protocol for the infusion set. A detection device operatively connected to the infusion device detects the signaling component and identifies the administration protocol. The infusion device is then configured to operate according to the administration protocol.

17 Claims, 5 Drawing Sheets

INFUSION DELIVERY SYSTEM

PRIORITY CLAIM

This patent application claims the benefit of U.S. Provisional Application No. 60/649,396, filed on Feb. 1, 2005 incorporated in its entirety.

BACKGROUND

The present disclosure relates to an infusion system and method that detects a signaling component identifying an administration protocol for an infusion set and conveys the administration protocol to an infusion device, and, in particular, to an infusion system wherein a signaling component identifying the administration protocol is disposed on at least an infusate source, an infusate tube, or an infusate tube slide clamp, the signaling component detected by an infusion device which is configured to operate according to the detected administration protocol.

Infusion treatment is a common medical practice for delivering a medicament to a patient. Infusion treatment typically entails delivering a fluid infusate, either parenterally or enterally, to a patient with an infusion device, most commonly an infusion pump. The infusate is typically provided by an infusion set having an infusate source, an infusate tube extending from the infusate source and a slide clamp adapted to receive the infusate tube. The slide clamp, which assists with infusate flow regulation, and the infusate tube when connected to the infusion pump place the infusate in fluid communication with the infusion pump.

Delivery of the infusate to the patient typically involves the physical and/or mechanical manipulation of the infusate tube by the infusion pump. Conventional infusion pumps customarily include parameters that may be adjusted in order to adapt to specific infusion set administration protocols delivery requirements. The parameters may include settings to accommodate the composition of the infusate, the physical and/or material properties of the infusate tube and the flow rate for effective infusate delivery, for example. The parameters may also include settings to accommodate the use of a special set compatible with a specific infusate, or to accommodate the use of a special set including a specific set component such as a particular valve or sensor.

As the number and sophistication of infusion set delivery requirements and concomitant infusion pump settings has increased, so too has the likelihood increased for a mismatch between the infusion set delivery requirements and the infusion pump settings. Such a mismatch may be highly injurious and potentially lethal to the infusion treatment patient. To further complicate matters, infusion pumps are typically undedicated, portable medical resources moved between different patients in a health care facility. Left unchecked, the infusion pump settings for one patient may be highly dangerous to a subsequent patient in need of the infusion pump. Relying on already overburdened health care professionals to ensure every infusion set delivery parameter is properly set on the infusion pump does not reduce the risk of mismatch between the infusion set requirements and the infusion pump settings to an acceptable level.

A need therefore exists to reduce the risk of inaccurate and dangerous delivery of an infusate to a patient. A need further exists for an automated infusion delivery system that automatically adjusts the infusion pump settings according to the infusion set delivery requirements thereby ensuring the proper delivery of the infusate by the infusion pump. A need further exists for a convenient, automated infusion system that permits patient self-administration of infusion treatment either at a health care facility or in the home.

SUMMARY

In accordance with the present disclosure, a system for delivering infusate to a patient is provided. The system includes an infusion device, an infusion set having an infusate source and a tube extending from the infusate source for delivering the infusate to the infusion device. The system further includes a slide clamp corresponding to the infusion set and having an aperture to receive the tube. A signaling component is disposed on the slide clamp. The signaling component identifies an administration protocol for the infusion set. A detection device determines the administration protocol identified by the signaling component. The detection device subsequently generates a signal based on the administration protocol. A controller, which is operatively connected to the infusion device, receives the signal. The controller is adapted to configure the infusion device to operate according to the administration protocol. The automatic conveyance of the administration protocol and subsequent configuration of the infusion pump to operate in accordance with the administration protocol dramatically reduces the likelihood of an erroneous or an inaccurate delivery of the infusate by the infusion pump.

In accordance with one aspect of the present disclosure, the signaling component may be disposed on a surface of the slide clamp, within the slide clamp, or may be disposed both on and within the slide clamp. The signaling component may be affixed to the slide clamp as is commonly known in the art including adhesive attachment, heat bonded, ultrasonic welding, insert molded or by a swaged attachment.

In accordance with another aspect of the present disclosure, the system has the ability to identify from one to about 64 or more different administration protocols by varying the signaling component. Correspondingly, the detection device is also adapted to differentiate between and detect from about one to about 64 or more different administration protocols.

In accordance with another aspect of the present disclosure, the detection device may be either a component of the infusion device or a remote detection device that may be positioned at a remote location relative to the infusion device. As a component of the infusion device, the detection device is preferably positioned proximate to a port adapted to receive the slide clamp.

Alternatively, the remotely located detection device may further be a hand-held device, such as a personal data assistant, adapted to be portably maneuvered proximate to the slide clamp in order to scan the signaling component. The detection device may be operatively connected to the controller as is commonly known in the art including by such non-limiting examples as an infrared connection, a microwave connection, a radio frequency connection, an electrical connection, a Bluetooth connection, a LAN network connection, a WAN network connection, an Internet connection, a universal serial bus connection and combinations thereof.

In accordance with another aspect of the present disclosure, the administration protocol may include infusion set delivery information selected from the group consisting of infusion route type, infusate delivery type, infusate tube composition, infusate flow rate, infusate quantity, infusate dosing unit, infusate dosing duration, infusate dosing volume, infusion duration, multiple infusate sources, multiple infusate mixing, secondary infusion administration, and combinations thereof. Preferably, the administration protocol may also be a predetermined administration protocol including a preselected set of any of the aforementioned information or infusion set delivery data. The administration protocol is preferably identified as an alpha-numeric character or representation by the signaling component wherein the alpha-numeric representation identifies a specific predetermined administration protocol to the detection device.

In accordance with another aspect of the present disclosure, the signaling component may be an optical signaling component, an electrical signaling component, a radio frequency signaling component, a magnetic signaling component, a thermal signaling component, an ultrasonic signaling component, a mechanical signaling component and combination thereof. In an embodiment, the detection device may correspond to the type of signaling component. Thus, the detection device may be an optical detection device, an electrical detection device, a radio frequency detection device, a magnetic detection device, a thermal detection device, an ultrasonic detection device, a mechanical detection device, and combinations thereof.

In an embodiment, the optical signaling component may be a bar code, a reflective material, a fluorescent or phosphorescent material, a reflective foil, a metal component, a color, a translucent or transparent material, printing, etching, ink, an ink printed code, UV ink or pigment, infrared ink or pigment, adhesive ink, an adhesive, a burn mark, a laser mark, a heat marking, an arrangement of holes extending through the slide clamp, an arrangement of protrusions extending from a slide clamp surface, an arrangement of indentations disposed on a portion of a slide clamp surface, and an arrangement of protrusions and indentations disposed on a slide clamp surface, and combinations thereof. The printing may be pad or ink jet printing. In addition to physical or mechanical marking or etching, the etching may be laser etching of the slide clamp material, or etching of laser reactive printed ink. In this aspect of the disclosure, the detection device is an optical detection device suitably adapted to detect the optical signaling component and identify the administration protocol therefrom.

The optical signaling component may be a bar code, such as a Universal Product Code, and may be detectable by a bar code reader. The optical signaling component may be an arrangement of holes extending through the slide clamp, an arrangement of protrusions and/or indentations on a surface of the slide clamp, detectable by an optical detection device having a light emitter and a light receiver such as a linear optical array or a laser light source. The optical signaling component may further be a color, an ink printed code, an ultraviolet ink printed code, or a reflective material with a respective optical detection device adapted to detect the color, the ink, the ultraviolet ink or the reflective material and identify the administration protocol therefrom.

In accordance with a further aspect of the present disclosure, the signaling component may be an electronic signaling component and the detection device is configured to detect the electronic signaling component. The electronic signaling component may preferably be composed of an electrical conducting material having an electrical resistance. A distinct administration protocol may then be associated with, assigned to, or otherwise identified by the electrical resistance of the electronic signaling component. The detection device may then be suitably adapted to detect the electrical resistance and identify the appropriate administration protocol based on the electrical resistance of the electronic signaling component. Detection may occur by contact between the electrical signaling component and the electrical detection device.

In accordance with another aspect of the present disclosure, the signaling component may be a radio frequency signaling component, preferably a radio frequency tag, and the detection device is a radio frequency detector, preferably a radio frequency interrogator. Administration protocol information may then be preprogrammed into the memory of the radio frequency signaling component as is commonly known in the art. As this radio frequency signaling component is capable of storing and conveying large amounts of data to the radio frequency detector, the radio frequency signaling component is particularly advantageous for use with administration protocols having detailed data or otherwise large amounts of infusion set delivery requirements.

In accordance with another aspect of the present disclosure, the signaling component may be an ultrasonic signaling component and the detection device is adapted to detect the ultrasonic signaling component and is preferably an ultrasonic transducer. The ultrasonic signaling component preferably has at least one property such as a density, a shape, a geometry and an orientation on/in the slide clamp. A property or a combination of properties of the ultrasonic signaling component may be varied to provide detection differentiation between ultrasonic signaling components. A distinct administration protocol may then be associated with or identified by each distinct ultrasonic signaling component.

In accordance with another aspect of the present disclosure, the signaling component may be a magnetic signaling component and the detection device may be adapted to detect the magnetic signaling component. The magnetic detection pattern of the magnetic signaling component may be altered by the density, composition, shape, size, geometry or orientation of the magnetic signaling component. A distinct administration protocol may then be assigned to or otherwise identified by a distinct magnetic detection pattern.

In accordance with another aspect of the disclosure, the signaling component may be a thermal signaling component and the detection device may be adapted to detect the thermal signaling component. The thermal signaling component may be a thermal stamp, a thermal transfer, a burn mark, or a heat marking that provides a unique optical to the detection device. The detection device may be an optical detection device or a thermal detection device that detects the signal from the thermal signaling component.

In accordance with another aspect of the present disclosure, a slide clamp for use with an infusion device and an infusion set is provided. The slide clamp includes a body having an aperture adapted to receive the infusate tube of the infusion set. The slide clamp further includes a signaling component configured to communicate information indicative of an administration protocol for the infusion set to a detecting device operatively connected to the infusion device. The signaling component may be an optical signaling component, an electrical signaling component, a radio frequency signaling component, an ultrasonic signaling component, a magnetic signaling component as previously discussed.

In an embodiment, the signaling component may be one or more protrusions, one or more indentations, or combinations thereof. The detection device may be a mechanical detection device that physically contacts the slide clamp to determine the presence or absence of a protrusion and/or indentation.

The signaling component may be affixed to a slide clamp body surface as is commonly known in the art with a heat bond, adhesive material, ultrasonic weld, a press interference fit or a swaged attachment being preferred. The signaling component may also include a plurality of legs corresponding to a plurality of openings disposed on a slide clamp surface. The legs may be inserted into the openings to secure the signaling component to the slide clamp. Alternatively, the signaling component may be disposed within the slide clamp body. This is accomplished preferably by insert molding the signaling component within the interior of the slide clamp. In an embodiment, the slide clamp may be made of or otherwise contain a material such as polypropylene, polyethylene, PVC acetyl resin, polyester, glycolized polyester, polycarbonate, acrylonitrile butadiene styrene, titanium dioxide, and combinations thereof. The slide clamp may also include other additives such as pigments or any other material or additive generally used in connection with the manufacture of slide clamps.

In accordance with yet a further aspect of the present disclosure, a system for delivering an infusate to a patient is provided, the system including an infusion set, and an infusion device. A signaling component identifying an administration protocol may be disposed on any component of the infusion set, namely, the infusate source, the infusate tube, the injection site, the slide clamp, a catheter or other component. The infusion device is suitably adapted to detect the signaling component, determine or otherwise identify the administration protocol, and operate according to the administration protocol. The signaling component may be an optical signaling component, an electrical signaling component, a radio frequency signaling component, an ultrasonic signaling component, or a magnetic signaling component. It is understood that the infusion device is suitably adapted to detect the signaling each respective signaling component.

In accordance with a further aspect of the present disclosure, a method for delivering an infusate to a patient with an infusion set and an infusion device is provided. The infusion set includes an infusate source component, an infusate tube component extending from the infusate source component, and a slide clamp component with an aperture adapted to receive the infusate tube component. A signaling component is provided on a component of the infusion set, the signaling component configured with information indicative of an administration protocol for the infusion set. The method further includes detecting the signaling component with a detection device, determining the administration protocol identified by the signaling device, and operating the infusion device according to the administration protocol.

In an embodiment, the detection device determines the administration protocol identified by the signaling device and generates a signal based on the administration protocol. The signal may be sent to a controller operatively connected to the infusion device which configures the infusion device according to the signal.

The method may further include affixing the signaling component to a surface of the infusate source, the infusate tube, or the slide clamp by heat bonding, ultrasonic bonding, adhesively bonding or swaging. Alternatively, the signaling component may be insert molded within the interior of the slide clamp.

The method may further include providing an arrangement of holes through the slide clamp component such that each hole permits the passage of light through the slide clamp. The administration protocol may then be identified by the number of holes in the arrangement, or the location of holes in the arrangement, or a combination of the number of holes and the location of holes in the arrangement. Alternatively, the method may include providing an arrangement of protrusions and/or indentations on a surface of the slide clamp and identifying the administration protocol by the number of protrusions/indentations in the arrangement, or the location of protrusions/indentations in the arrangement, or a combination of the number of protrusions/indentations and the location of the protrusions/indentations in the arrangement.

The method may further include detecting an optical signaling component, an electronic signaling component, a magnetic signaling component, a radio frequency signaling component, an ultrasonic signaling component a mechanical signaling component and combinations thereof, with a respective optical detection device, an electronic detection device, a magnetic detection device, a radio frequency detection device, an ultrasonic detection device a mechanical detection device and combinations thereof. The detection may occur proximate to the infusion device, within the infusion device or at a location remote from the infusion device.

These and other aspects and attributes of the present disclosure will be discussed with reference to the following drawings and accompanying description.

Additional features and advantages of the present disclosure are described in, and will be apparent from, the following Detailed Description of the disclosure and the figures.

DETAILED DESCRIPTION

Figure 1:
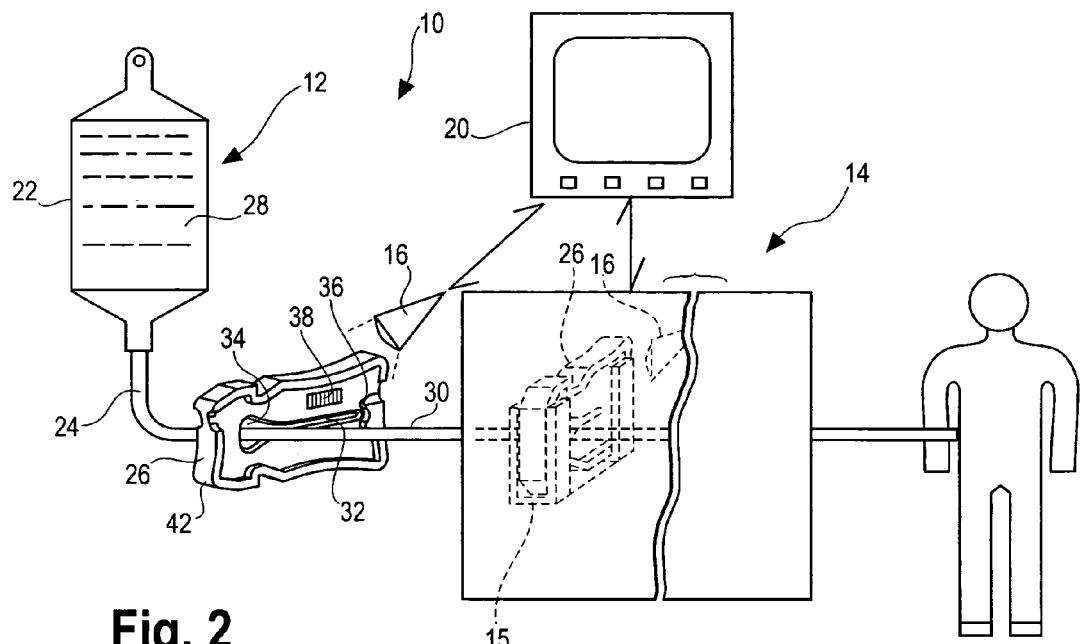
FIG. 1 is a schematic representation of an infusion delivery system in accordance with the present disclosure.

Referring to the figures generally, where reference numerals denote like structure and elements, and in particular to FIG. 1, an infusion delivery system 10 for delivering an infusate to a patient is shown. Infusion delivery system 10 includes an infusion set 12, an infusion device 14, a detection device 16 which generates a signal 18 and a controller 20. Infusion set 12 includes an infusate source 22, an infusate tube 24 extending from infusate source 22, and a slide clamp 26.

Infusion device 14 may be any medical device capable of pumping a fluid into a patient as is commonly known in the art. Non-limiting examples of such devices include cassette pumps and peristaltic pumps. It is preferred that infusion device 14 be a medical device capable of delivering fluids to a patient peristaltically. An example of a peristaltic infusion device is described in U.S. Pat. No. 6,123,524, which is incorporated by reference herein. Infusion device 14 further includes a port 15 for receiving slide clamp 26.

An infusate 28 is contained in infusate source 22. Infusate source 22 may be composed of glass or a rigid or flexible container composed of a polymeric material as is commonly known in the art. Infusate 28 may be any fluid or any fluid medicament that is administered by an infusion device. Examples of infusate 28 include, but are not limited to, saline or dextrose solutions, nutritional solutions, dialysis solutions, blood, blood components, blood substitutes and the like.

Infusate tube 24 extends from infusate source 22 and has a distal end 30 that is suitably adapted to connect to infusion device 14. Infusate tube 24 thereby provides a passage or a fluid connection enabling the delivery of infusate 28 to infusion device 14. The skilled artisan will appreciate that infusate tube 24 may be composed of a collapsible, flexible polymeric material. The composition of infusate tube 24 may the same as or different from the composition of infusate source 22.

Infusion set 12 further includes slide clamp 26 having an aperture 32 adapted to receive infusate tube 24. Aperture 32 includes a wide portion 34 and a narrow portion 36. One of ordinary skill in the art will appreciate that infusate may flow through infusate tube 24 when infusate tube 24 is received in wide portion 34 while infusate is prevented from flowing through infusate tube 24 when infusate tube 24 is received in narrow portion 36. Slide clamp 26 further includes a body 40 and a peripheral lip 42. Slide clamp 26 may be made from any rigid material including, but not limited to, wood, metal or a polymeric material with a polymeric material being preferred.

In an embodiment, slide clamp 26 may be made of a plastic material such as polypropylene, and is injection molded. Slide clamp 26 may also be made from a glycolized polyester such as PETG, co-polyester, an acetyle resin such as DEL-RIN®, or any other suitable material that is capable of maintaining close manufacturing tolerances, can withstand pressures within infusate tube 24, and can withstand various sterilization techniques, including gamma and EtO sterilization, without impairing the functionality of slide clamp 26. In an embodiment, slide clamp 26 may be made from a polyethylene such as a high density polyethylene (HDPE) and optionally additives as explained more fully below.

A signaling component 38 is disposed on slide clamp 26 by any suitable arrangement as is commonly known in the art. Consequently, "disposed" means that signaling component 38 may be located or otherwise positioned on, onto, in, within, or through slide clamp 26. The term "disposed" may further mean a position encompassing a combination of the aforementioned positions. Thus, a portion of signaling component 38 may be located on slide clamp 26 while another portion of signaling component 38 may be located within slide clamp 26 as will be described more fully below.

Signaling component 38 identifies an administration protocol for infusion set 12. The administration protocol may include any information related to, associated with or corresponding to the delivery of infusate 28 to the patient. Consequently, the administration protocol may include any instructions, information, parameters, indicators, directions, identifiers, indicia, data, or directives associated with infusion set 12 and infusion device 14.

Non-limiting examples of information identified by the administration protocol include infusion route type, infusate delivery type, infusate delivery temperature, infusate type, infusate tube composition, infusate flow rate, infusate quantity, infusate dosing unit, infusate dosing duration, infusate dosing volume, infusion duration, multiple infusate sources, multiple infusate mixing, secondary infusion administration, and combinations thereof. The administration protocol may also include patient information such as patient name, age, gender, height, weight, type of therapy, type of disease and type of condition of patient, for example.

Non-limiting examples of infusion route type include intravenous, parenteral, enteral, epidural subcutaneous, intramuscular, or other routes of medication administration. Infusion delivery type may identify dosing information such as continuous infusion, alternating infusions, sequencing infusions, tapering infusions, secondary infusate or piggyback parameters, infusate drip rate, and titrating infusions. Infusate delivery type may further include information regarding the composition of the infusate tube and physical properties such as tensile strength, modulus of elasticity, melting point or geometry, size, material type, or features or components of the tubing relating to appropriate drug solution compatibility or route of infusion. Infusate type may identify the composition of the infusate fluid or fluids or indicate whether a plurality of infusate fluids is to be delivered during the infusion session.

In addition, the administration protocol may include diagnostic information. The diagnostic information may be used to perform diagnostic tests or routines on the infusion device or any other component of the infusion system. For example, a diagnostic infusion set may include an infusate source containing a particular fluid to be used in the testing, wherein expected operational parameters of the infusion device based on the particular fluid may be used as a diagnostic benchmark.

Detection device 16 of system 10 may be any device capable of detecting signaling component 38 as is commonly known in the art. Detection device 16 detects or otherwise determines the administration protocol identified by signaling component 38. Detection device 16 may be a component of or otherwise be integral to infusion device 14. Alternatively, detection device 16 may be located at a location remote from infusion device 14. Detection device 16 may also be a portable detection device. As a portable detection device, detection device 16 may be removable from a housing of infusion device 14.

Upon detection of signaling component 38, detection device 16 generates signal 18 that is based on the administration protocol identified by the signaling component. Detection device 16 subsequently sends signal 18 to controller 20. Upon reception of signal 18, controller 20 deciphers the signal, identifies and interprets the administration protocol. Controller 20 is operatively connected to infusion device 14 and is further adapted to configure infusion device 14 to operate according to the administration protocol.

Controller 20 preferably includes a processor to process the administration protocol information contained in signal 18. Controller 20 may be a component of infusion device 14. Alternatively, controller 20 may be located at a location remote from infusion device 14. Controller 20 may further include a display 21 that displays and/or prompts or otherwise notifies information regarding the administration protocol to a health care professional or the patient.

The administration protocol is typically a predetermined administration protocol represented by an alpha-numeric character but may be representable by other identifiers such as a binary code or UPC code or some other engineered code as is known in the art. The alpha-numeric character represents a predetermined set of infusate administration parameters to be sent to the infusion device. Upon reception of signal 18, controller 20 is programmed to recognize the predetermined administration protocol represented by the alpha-numeric character. Controller 20 then configures infusion device 14 according to these predetermined parameters.

For example, an alpha-numeric representation of "12" may be predetermined to identify an administration protocol for delivery of a standard parenteral saline solution of 500 ml at a flow rate of 2.6 ml/min. Upon detection of the alpha-numeric representation "12" by detection device 16 and subsequent reception of the signal carrying the alpha-numeric representation of "12" by controller 20, controller 20 processes the administration protocol from the signal and configures infusion device 14 to the predetermined settings denoted by the alpha-numeric character "12" (i.e., the controller initiates the parenteral tube port and sets the pump and timing components for a flow rate of 2.6 ml/min). System 10 is preferably adapted to identify from one to about 64 or more different predetermined administration protocols.

In accordance with one aspect of the present disclosure, signaling component 38 is an optical signaling component as shown in FIGS. 2-11. Non-limiting examples of suitable optical signaling components include a bar code, a reflective material, a fluorescent or phosphorescent material, a reflective foil, a metal component, a color, a translucent or a transparent material, printing, etching, ink, an ink printed code, ultraviolet (UV) ink or pigment, infrared (IR) ink or pigment, adhesive ink, an adhesive, a burn mark, a heat marking, a laser mark, an arrangement of holes extending through the slide clamp, an arrangement of protrusions extending from a slide clamp surface, an arrangement of indentations disposed on a portion of a slide clamp surface, and an arrangement of protrusions and indentations disposed on a slide clamp surface. Regardless of the specific embodiment of the optical signaling component, it is understood that detection device 16 is suitably adapted to detect the optical signaling component.

Figure 2:
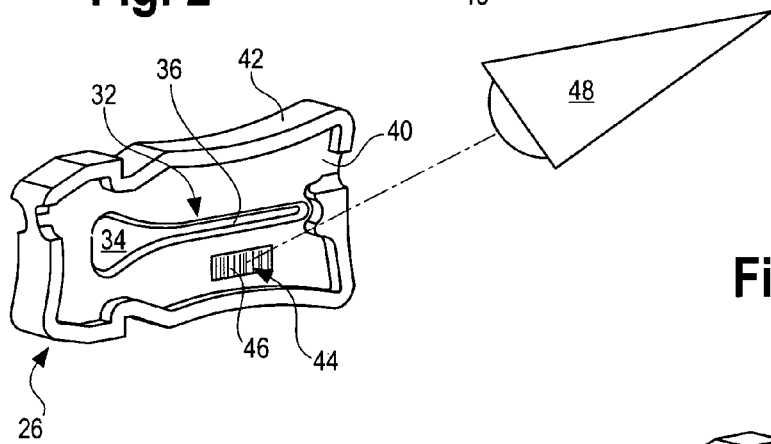
FIG. 2 is a perspective view of a slide clamp having an optical signaling component and an optical detection device in accordance with the present disclosure.

In accordance with one aspect of the present disclosure, FIG. 2 depicts an optical signaling component 44 and may be a bar code 46. Bar code 46 may be any bar code capable of being encoded with the administration protocol information as is commonly known in the art with a Universal Product Code (UPC) being preferred. Preferably, bar code 46 identifies an alpha-numeric character which represents a predetermined administration protocol. A bar code reader 48 may detect bar code 46, generate a signal based on the administration protocol and send the signal to controller 20. Bar code reader 48 may or may not be a component of infusion device 20. Preferably, bar code reader 48 is a portable device electronically connected to controller 20.

Figure 4:
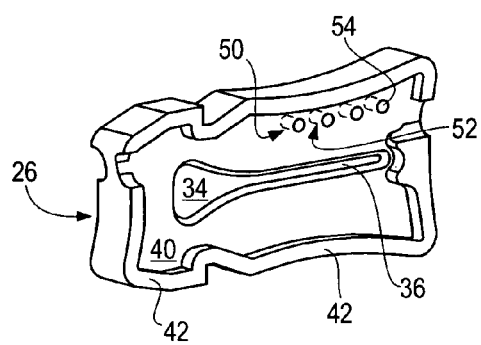
FIG. 4 is a perspective view of an embodiment of the optical signaling component of FIG. 3.
Figure 3:
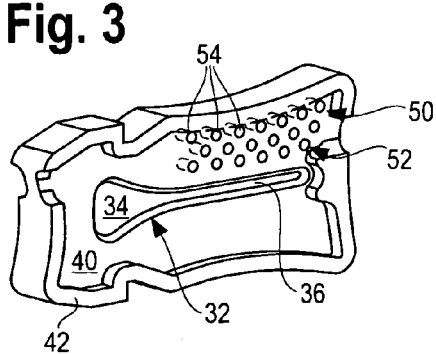
FIG. 3 is a perspective view of an embodiment of a slide clamp having an optical signaling component.

In accordance with another aspect of the disclosure, an optical signaling component 50 is an arrangement 52 of holes 54 as shown in FIG. 3. In this embodiment, slide clamp 26 is formed to include a plurality of holes 54 that extend through slide clamp body 40. Holes 54 may be formed through slide clamp 26 in any manner as is commonly known in the art. Preferably, slide clamp 26 is made from a polymeric material and a projection heated above the melting point of the polymeric material such as a hot probe is used to penetrate entirely through body 40 of slide clamp 26. Alternatively, holes 54 may be punched through body 40 with a hole punch machine, formed by a laser, or formed during molding of slide clamp 26. Holes 54 may also be formed through any portion of lip 42 in a similar manner. Holes 54 may be any shape that allows light to pass through the holes such as polygonal, elliptical, slot shaped and circular, with circular being preferred. Arrangement 52 may have any desired shape, geometry, or alignment pattern of holes 54. Arrangement 52 may be a rectangular array of holes as shown in FIG. 3. Alternatively, optical signaling component 50 may be an arrangement 52 of linearly aligned holes 54 as shown in FIG. 4.

Holes 54 are formed to permit passage of light through slide clamp 26. The position of holes 54 in arrangement 52 may determine the administration protocol. Alternatively, the number of holes 54 in arrangement 52 may also identify the administration protocol. In addition, the position as well as the number of holes 54 in arrangement 52 may identify the administration protocol. Preferably, arrangement 52 identifies an alpha-numeric representation of a predetermined administration protocol.

Figure 5:
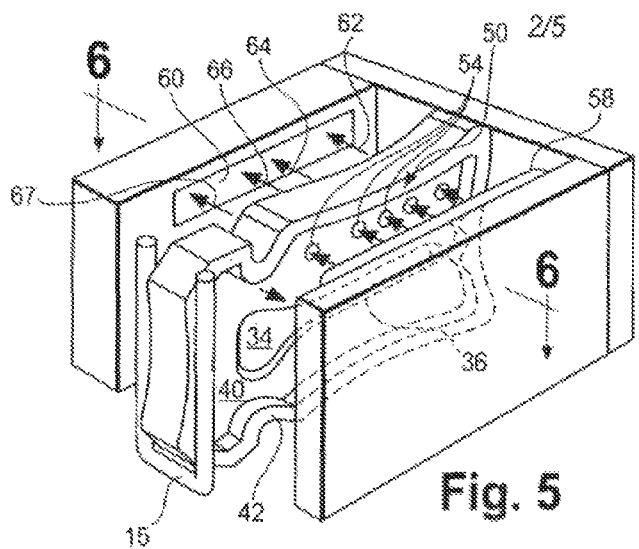
FIG. 5 is a fragmentary perspective view of a portion of the infusion device of FIG. 1 illustrating a slide clamp having an optical signaling component and a detection device in accordance with an embodiment of the present disclosure.
Figure 6:
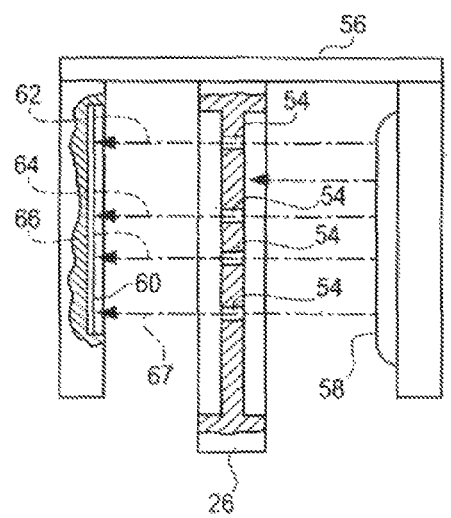
FIG. 6 is a sectional view of the slide clamp and detection taken along line 6-6 device of FIG. 5.
Figure 5A:
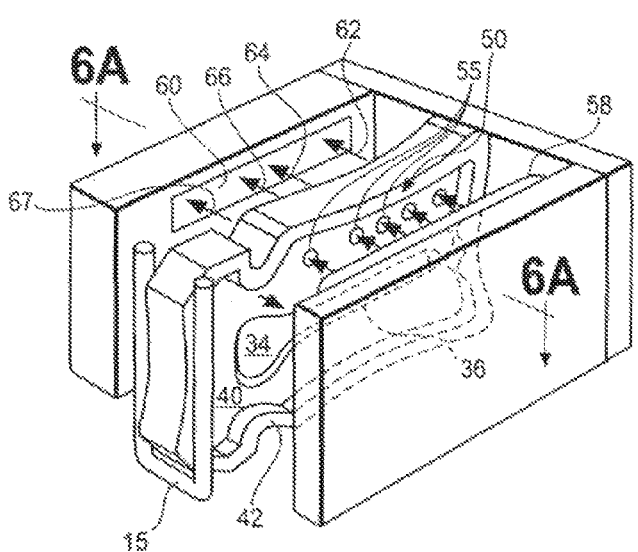
FIG. 5A is a fragmentary perspective view of a portion of the infusion device of FIG. 1 illustrating a slide clamp having an optical signaling component and a detection device in accordance with an embodiment of the present disclosure.
Figure 6A:
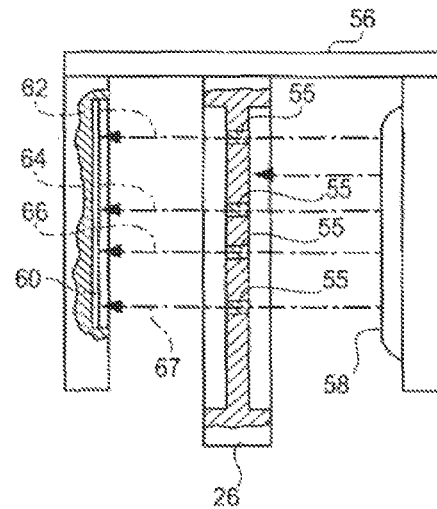
FIG. 6A is a sectional view of the slide clamp and detection taken along line 6A-6A device of FIG. 5A.

In an embodiment, optical signaling component 50a may include slide clamp 26 having a plurality or an arrangement of transparent areas 55 as shown in FIG. 5A. Transparent areas 55 may be a transparent material or a translucent material, including such nonliming examples as translucent polymeric material or glass. Transparent areas 55 may permit the transmission of light while the rest of the slide clamp body may be made of an opaque material or a material not transmissive to light as shown in FIG. 6A. The number and/or position of transparent areas 55 about the slide clamp may identify the administration protocol. A slide clamp containing transparent areas 55 may be formed by a two-shot molding process as is commonly known in the art. A first mold shot may inject opaque material into the slide clamp mold followed by a second mold shot of a transparent polymeric material to form the transparent areas.

Optical detection device 56 is utilized to detect optical signaling component 50 as shown in FIG. 5. Optical detection device 56 is preferably a component of infusion device 14 disposed adjacent to slide clamp port 15 although optical detection device may be located remote from infusion device 14. Optical detection device 56 may be a linear optical array, a laser light source or similar device as is commonly known in the art. Detection device 56 includes a light emitter 58 and a light receiver 60. When slide clamp 26 is situated in port 15, light emitter 58 emits light through holes 54 as shown in FIGS. 5 and 6. Light receiver 60 is disposed on an opposing side of slide clamp 26 and positioned to detect light from emitter 58, the light passing through holes 54 and forming light beams 62, 64, and 66. Thus, the number and arrangement (i.e., the presence or absence of a light beam) of light beams 62, 64 and 66 due to the presence or absence of a hole in a predetermined position may be used to denote a particular value. Optical detection device 56 may detect optical signaling component 50a (FIGS. 5A & 6A) in a similar manner. For example, light emitted from light emitter 58 through transparent areas 55 may be detected by light receiver 60.

For example, the reception/non-reception of light beams 62, 64, and 66 may translate to a 1,1,0,1 detection pattern ("1" for reception of light beam, "0" for no light beam reception) as shown in FIG. 5. Such a pattern may denote a numeric representation such as a binary value of 1101. An additional light beam 67 may serve as a parity bit for error detection. The binary value 1101 may then be used to represent a predetermined administration protocol to controller 20. In this manner, optical detection device 56 is thereby adapted to identify the administration protocol based on the number light beams, the arrangement of light beams or the combination of the number and arrangement of light beams received by light receiver 60.

Figure 7:
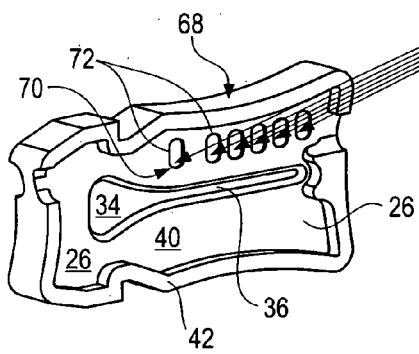
FIG. 7 is a perspective view of a slide clamp having an optical signaling component and an optical detection device in accordance with an embodiment of the present disclosure.
Figure 8:
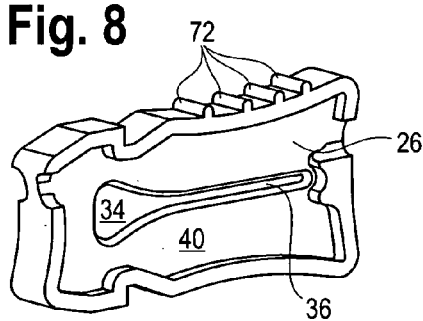
FIG. 8 is a perspective view of an embodiment of the optical signaling component of FIG. 7.

In accordance with another aspect of the disclosure, optical signaling component 68 may be an arrangement 70 of protrusions 72 as shown in FIGS. 7 and 8. Protrusions 72 extend from a surface of slide clamp body 40 (FIG. 7) or the exterior surface of lip 42 (FIG. 8). An optical detection device 74 is adapted to detect the presence of protrusions 72 and the distance between protrusions 72 as is commonly known in the art.

As similarly discussed with arrangement 52, the number of protrusions 72 in arrangement 70 or the location of protrusions 72 in arrangement 70 may be used to identify the administration protocol. In addition, a combination of the number and location of protrusions 72 in arrangement 70 may be used to identify the administration protocol. It is preferred that at least one protrusion serves to indicate a parity bit to optical detection device 74 in order to prevent an erroneous detection.

Figure 9:
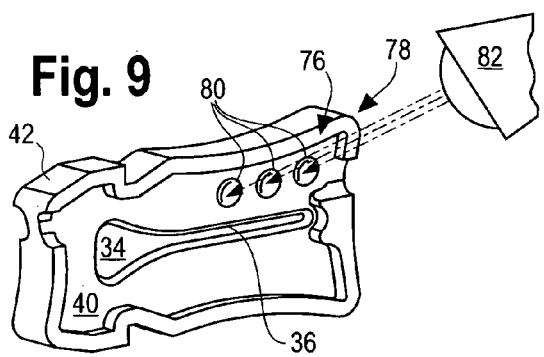
FIG. 9 is a perspective view of a slide clamp having an optical signaling component in accordance with an embodiment of the present disclosure.

In accordance with another aspect of the disclosure, an optical signaling component 76 includes an arrangement 78 of indentations 80 as shown in FIG. 9. Indentations 80 may be any crevice, divot, cavity, impression, dent, depression, or pit extending inward from the surface of body 40 or the surface of lip 42. An optical detection device 82 is adapted to emit light onto slide clamp 26 and detect and differentiate between the darker bands of light reflected from indentations 80 compared to the lighter bands of reflected light from the non-indented surfaces of slide clamp 26. Slide clamp 26 is preferably white in color to enhance the contrast between the darker light reflected from indentations 80 and the light reflected from the non-indented slide clamp surfaces. Preferably, optical detection device 82 is a component of infusion device 14 proximate to port 15. Most preferably, optical detection device 82 is a linear optical array with light emitters and light receivers disposed on the same side of side clamp port 15. Optical signaling component 76 is preferably scanned by optical detection device 82 when the slide clamp is secured in port 15.

Figure 11:
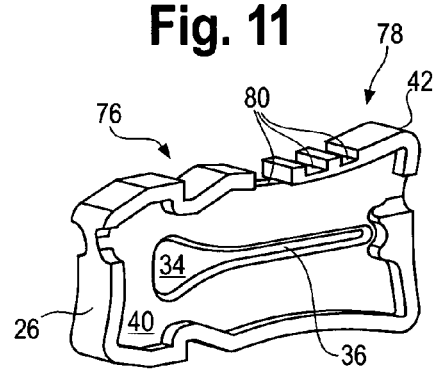
FIG. 11 is a perspective view of an alternate embodiment of the optical signaling component of FIG. 9.
Figure 10:
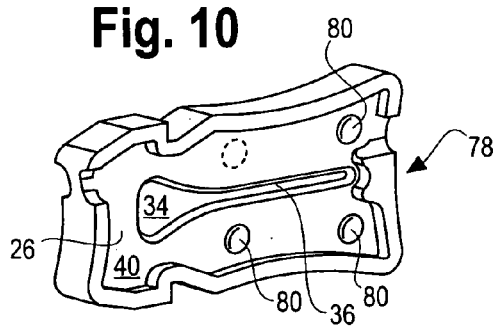
FIG. 10 is a perspective view of an embodiment of the optical signaling component of FIG. 9.

Indentations 80 may be disposed proximate to each other on the surface of body 40 as shown in FIG. 9. Alternatively, indentations 80 may be disposed at the corners of slide clamp 26 as shown in FIG. 10. Indentations 80 may also be disposed on a surface of peripheral lip 42 as shown in FIG. 11. The number of indentations, the position of the indentions, or a combination of the number and position of indentations in arrangement 78, may identify a particular administration protocol as previously discussed. In an embodiment, the one, some or all of the protrusions and/or indentations may be coated with an ink to provide further contrast between the protrusions and indentations. In a further embodiment, the protrusions may include a first ink and the indentations may include a second ink that contrasts the first ink.

Figure 11A:
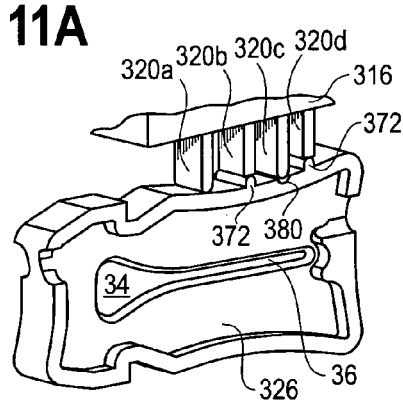
FIG. 11A is a perspective view of a signaling component and a detection device in accordance with an embodiment of the present disclosure.

In an embodiment, the arrangement of protrusions, and/or the arrangement of indentations may be mechanical signaling components. The protrusions and/or indentations may be positioned anywhere on the slide clamp (i.e., body or lip) as previously discussed. It is understood that the arrangement may include a single protrusion, a single indentation, a plurality of protrusions, a plurality of indentations, and a combination of one or more protrusions with one or more indentations. A detecting device such as a mechanical detecting device may be used to detect the presence or the absence of a protrusion and/or an indentation. In an embodiment, slide clamp 326 has protrusions 372 and indentation 380 on a lip surface thereof as shown in FIG. 11A. Although the protrusions and indentation are shown on a lip of the slide clamp, it is understood that the protrusions/indentations may be located anywhere on the slide clamp. Mechanical detection device 316 includes probes 320a, 320b, 320c, and 320d that physically contact slide clamp lip 342. Contact between the probes and a protrusion may force the probe to retract as shown by the retracting motion of probes 320b and 320d. This retracting motion may trigger a switch to elicit detection of the protrusions. Similarly, the presence of an indentation proximate to the probe may permit the probe to extend as shown by the extension of probe 320c. This extending motion of the probe may trigger a switch to thereby elicit detection of the indentation. The mechanically detected protrusion/indentation profile may be compared to predetermined profiles representing corresponding administration protocols. It is understood that a single protrusion or indentation or a plurality of protrusions and/or indentations may be the mechanical signaling component.

In an embodiment, the degree or extent to which the probe extends or retracts may be correspond to the detection of distinct administration protocols. Thus, the size of the protrusion and/or the depth of an indentation may be used to distinguish between different administration protocols. For example, detection of a large protrusion may correspond to a first protocol whereas detection of a smaller protrusion corresponds to a second administration protocol. The shallowness or depth of an indentation may identify or differentiate between respective different administration protocols in a similar manner.

In an alternate embodiment, a mechanical detection device may be used to detect the presence and/or absence of any combination of protrusions and/or indentations.

An optical signaling component composed of either protrusions 72 or indentations 80 is advantageous as the provision of either may occur during the manufacturing process of the slide clamp. The slide clamp mold may be configured to include either the protrusions or the indentations, for example. Thus, a signaling component composed of either protrusions or indentations eliminates the necessity for an additional step in the slide clamp manufacturing process.

The skilled artisan will recognize various other embodiments for the optical signaling component. For example, the color of the slide clamp may be associated with a predetermined administration protocol. The detection device may be adapted to detect and differentiate between a multitude of slide clamp colors. Alternatively, the slide clamp may be a plurality or a combination of colors detectable by the detection device. Each color or combination of colors may be may have a different reflective index, or light wavelength that may be utilized to indicate a corresponding administration protocol. The detection device may be adapted to detect and differentiate between the different reflective indices and/or wavelength of the light reflected from differently colored slide clamps. In an embodiment, the detection device may be a color sensing device such as a TAOS TCS230.

In a further embodiment, four or more colors, such as blue, red, yellow, and green, for example, may be used to identify four or more distinct administration protocols. A slide clamp containing one of these colors (i.e., a blue slide clamp, a red slide clamp, a yellow slide clamp, and a green slide clamp) may each provide a distinct reflectance profile when detected by a color sensing device. Utilizing color as the signaling component is advantageous as little or no molding modifications are required for slide clamp manufacture. The appropriate pigment merely needs to be added to the polymeric resin during slide clamp molding. In addition, no modifications are necessary for clamp restraint components used in conventional infusion systems.

In a further embodiment, the signaling component may be a laser mark. Titanium dioxide may be added to the polymeric resin material that is used to mold the slide clamp. A laser may then be used to etch the slide clamp to form a laser mark. The laser mark may be formed anywhere on the slide clamp, including the slide clamp body and the edge or rim of the slide clamp. Additionally, laser marking or etching may be utilized with a slide clamp or other set component not including titanium dioxide or other additive.

In an embodiment, addition of titanium dioxide to the material composition of the slide clamp forms a white colored slide clamp or otherwise lightens the color hue of the slide clamp. The laser etching forms one or more laser marks on the slide clamp surface, the laser marks being darker in color than the color of the slide clamp. Laser marking is advantageous as it is possible to form up to 100 or more distinct laser mark patterns which may correspondingly identify up to 100 or more different administration protocols.

In an embodiment, the slide clamp may be made of a polyethylene, such as HDPE. An additive may be added to the polyethylene to harden or soften the slide clamp as desired as is commonly known in the art. A laser may then be used to etch the slide clamp surface as previously discussed. In an embodiment, the laser may be a UV laser or a YAG laser or a $CO_2$ or other laser. In a further embodiment, the laser mark may be formed by way of a cold laser process as is commonly known in the art.

In an embodiment, a detection device, such as a linear photo array may be configured to detect the laser mark. The linear photo array may include an integrated sensor having a linear photodiode array, one or more LEDs or blue LEDs, and an optical lens that captures an image of the laser mark or laser pattern on the slide clamp. The image may then be compared to a database of predetermined marks, each mark corresponding to an administration protocol.

Figure 11B:
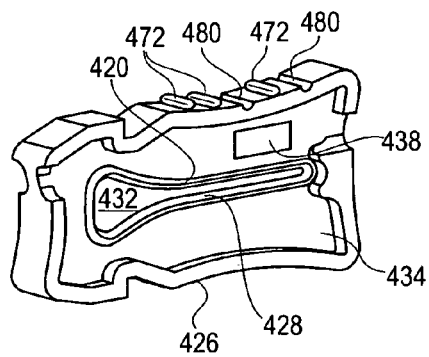
FIG. 11B is a perspective view of a slide clamp in accordance with an embodiment of the present disclosure.

In an embodiment, slide clamp 426 may include two or more materials as shown in FIG. 11B. Slide clamp may include an inner portion 428 having a soft, lubricious material that surrounds or substantially surrounds aperture 432. In an embodiment, inner portion 428 may be a polyethylene such as HDPE, a polypropylene, and combinations thereof. An outer portion 434 of slide clamp 426 may be composed of a harder or more rigid material. In an embodiment, outer portion 434 may be a polycarbonate, an acrylonitrile butadiene styrene, or a combination thereof. Outer portion 434 may or may not surround or substantially surround inner portion 428. In this configuration, the softer material may be compatible with tubing that extends through the aperture, thereby preventing scoring of the tubing. The hard outer material of outer portion 434 may provide a more suitable surface and provide better results when signaling component 438 is a print, a hot stamp, an ink print or code, a laser mark on the outer portion 434 of the slide clamp, as previously discussed. Slide clamp 426 may or may not include protrusions 472 and indentations 480. Additionally, the protrusions 472, indentations 480, or a combination of same may be formed by a two shot molding process as known in the art. The detection device may be any detection device as discussed herein. In an embodiment, the outer portion includes a laser mark that may be detectable with a linear photodiode array as previously discussed.

In an embodiment, the two-component slide clamp may be in a two shot mold process as is commonly known in the art. A two-shot molding process may include the provision of a mold in a single press having two cavities. The inner portion may define the first cavity and the outer portion may define the second cavity. Respective first and second polymeric resins may be deposited in the first and second cavities simultaneously or sequentially, as desired. The interface between the inner portion and the outer portion may include a chemical bond, a mechanical bond, and a combination thereof.

The optical signaling component may be ink and the detection device may be adapted to detect the ink. The ink may be applied to a surface of the slide clamp in the form of any indicia suitable to identify an administration protocol. Non-limiting examples of ink indicia include a pattern of lines and spaces, a pattern of dots and dashes, or an alpha-numeric character or characters. It is understood that the detection device may be suitably adapted to detect and determine the administration protocol from the ink indicia. In one embodiment, the ink may be an ultraviolet ink detectable by an ultraviolet detection device. Moreover, any reflective material that may be adapted to provide different reflective indices upon exposure to light may be utilized as an optical signaling component and is within the scope of the present disclosure. Furthermore, slide clamp 26 may be composed of translucent materials or a combination of translucent materials which may be used to provide a plurality of distinguishable material properties, such as light wavelength absorption, when exposed to the optical detection device.

In an embodiment, the optical detection device may be a TAOS (Texas Advanced Optical Solutions) linear array. The linear array may include a light source, a light guide, a lens array, a pixel reader, and an electrical connection to the controller. An optical barrier may be used to segregate the light source and light guide from the lens array and pixel reader. The light source may be used to emit light through the light guide which projects light onto the optical signaling component. The light is then reflected off the optical signaling component and passes through the lens array to the pixel reader. The pixel reader receives a light profile based on the particular optical signaling component (i.e., indentations, protrusions, bar code or ink) and transmits a signal corresponding to the received light profile to the electrical connection for further processing by the controller. Consequently, optical detection may occur as a result of light emitted onto and reflected from a single side of the slide clamp. This is advantageous as it requires the optical detection device to be positioned proximate to only a single side of the slide clamp.

Figure 12:
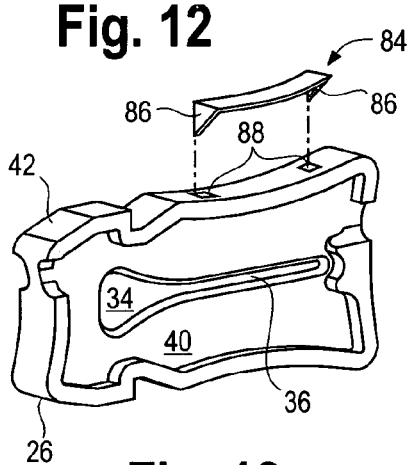
FIG. 12 is a exploded perspective view of a slide clamp having an electronic signaling component in accordance with the present disclosure.

FIG. 12 shows another embodiment of the disclosure wherein the signaling component may be an electronic signaling component 84. Electronic signaling component 84 may be composed of any electrically conducting material having an electrical resistance. A distinct administration protocol may be associated with or otherwise identified by a corresponding electronic resistance value. Consequently, when the detection device detects the resistance of electronic signaling component 84, either the detection device and/or the controller may be used to translate or otherwise associate the resistance value with the proper administration protocol. Electronic signaling components may be adapted to identify from one to about 64 or more different administration protocols. This may be done by varying the shape, size or the material composition of electronic signaling component 84 thereby varying the resistance of the electronic signaling component. In an embodiment, the slide clamp may be composed of an electrically conducting material the resistance of which may be detected or otherwise measured by the detection device. Thus, the detection device may be any device capable of detecting the electronic resistance of electronic signaling component 84 and/or slide clamp 26.

Electronic signaling component 84 may be a strip of electronically conducting material attached to a surface of slide clamp 26 as shown in FIG. 12. Non-limiting examples of suitable electronically conducting material may be any metal or any semiconducting material. Electronic signaling component 84 may further include legs 86. Legs 86 are adapted to fit into corresponding holes 88 disposed on a surface of the slide clamp thereby securing electronic signaling component 84 to slide clamp 26. Legs 86 may be secured in holes 88 with adhesive, friction fit, rivets screws or a swaged attachment by bending the legs after the legs are inserted into the holes. Alternatively, legs 86 may be sharp prongs to penetrate the material of the slide clamp. The skilled artisan will further appreciate that electronic signaling component 84 may be attached to slide clamp 26 with an adhesive material or by insert molding as is commonly known in the art.

Figure 13:
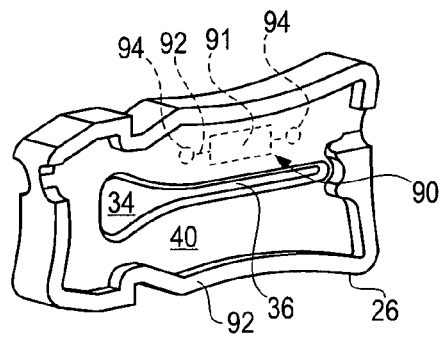
FIG. 13 is a perspective view of an alternate embodiment of the electronic signaling component of FIG. 12.

In an alternate embodiment, electronic signaling component 90 may be an electronic resistor 91 disposed within slide clamp 26 as depicted in FIG. 13. Electronic signaling component 90 may be placed within slide clamp 26 as is commonly known in the art with insert molding being preferred. Electronic signaling component includes a wire 92 which extends to the surface of slide clamp 26 exposing a pair of contacts 94 for electrical communication with the detecting device. Thus, detection of electronic signaling component 90 may occur by contacting the detection device with contacts 94 to determine the resistance of component 90.

Figure 14:
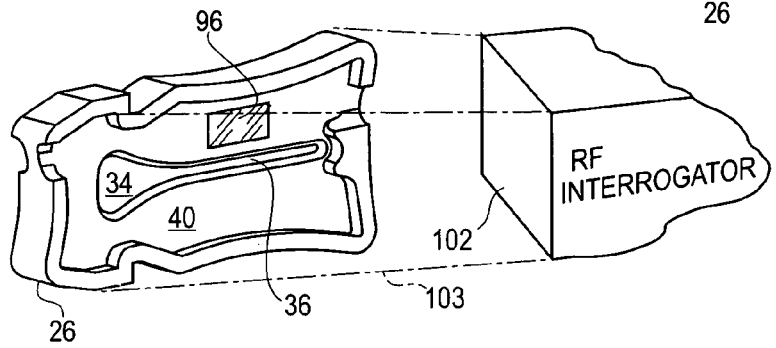
FIG. 14 is a perspective view of a slide clamp having a radio frequency signaling component and a radio frequency detection device in accordance with an alternate embodiment of the present disclosure.

In another aspect of the disclosure, the signaling component may be a radio frequency (RF) signaling component. Preferably, the radio frequency signaling component is a radio frequency identification (RFID) tag 96 as shown in FIG. 14. RFID tag 96 is capable of receiving, storing and transmitting information as is commonly known in the art. RFID tag 96 may include an antenna, circuitry for processing RF signals, a microprocessor, memory, and, optionally, a power supply. RFID tag 96 may be preprogrammed with administration protocol information or a predetermined administration protocol as is commonly known in the art. In a further embodiment, the RFID tag may be a chipless RFID tag. The chipless RFID tag may include antennae printed on a surface of the slide clamp or embedded in the slide clamp interior.

Figure 15:
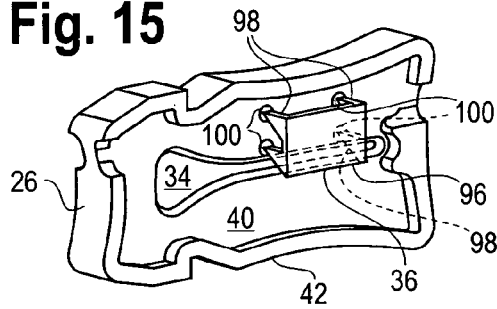
FIG. 15 is an exploded perspective view of an embodiment of the radio frequency signaling component of FIG. 14.

RFID tag 96 may be affixed to a surface of slide clamp 26 with an adhesive material or a heat bond as is commonly known in the art. Preferably, RFID tag 96 includes legs 98 which may be inserted into corresponding holes 100 disposed on body 40 to affix RFID tag 96 to slide clamp 26 as shown in FIG. 15. Legs 98 may be secured in holes 100 with an adhesive material, friction fit, rivets, screws or with a swaged arrangement whereby legs 98 are bent after insertion into holes 100. Alternatively, tag 96 may be insert molded into the interior of slide clamp 26.

RFID tag 96 may be a passive device or an active device. As a passive device, an RFID tag transmits a signal only upon reception of an RF interrogation signal utilizing operating power generated from the RF interrogator. As an active device, an RFID tag is configured with its own power supply and thereby capable of transmitting a signal independently. As passive RFID tags are smaller and lighter than active RFID tags, it is preferred that RFID tag 96 is a passive RFID device.

In this embodiment of the disclosure, the detection device is an RF detector adapted to detect RFID tag 98. Preferably, the RF detector is an RF interrogator 102 as shown in FIG. 14. RF interrogator 102 typically includes an antenna, a transceiver for transmitting an interrogation signal to and receiving a response signal from the RFID tag, and a decoder for reading the encoded information in the signal from the RFID tag. RF interrogator 102 generates an electromagnetic field 103 at a predetermined frequency. When RFID tag 96 enters the field, an electric current is induced providing power to RFID tag 96 and modulating the electromagnetic field to transmit the preprogrammed administration protocol data stored in the memory of RFID tag 96 back to RF interrogator 102. RF interrogator 102 then decodes this data and transmits the administration protocol data with signal 18 to controller 20.

System 10 including RFID tag 96 and RF interrogator 102 provides several advantages. A line-of-sight arrangement between signaling component 96 and RF interrogator 102 is not necessary for detection to occur. Consequently, RF interrogator 102 is well-suited to be located remote from controller 20, or serve as a portable or a hand-held detection device. It is understood, however, that RF interrogator 102 may be a component of infusion device 14.

Moreover, as no contact between signaling component 96 and RF interrogator 102 is required for detection, conditions otherwise deleterious to proper detection of the signaling component are eliminated. For example, a wet slide clamp or fluid, dust, dirt, or any other physical impediment disposed upon the slide clamp have no impact on the proper detection of RFID tag 96 by RF interrogator 102.

The skilled artisan will further recognize that the large memory capacity of RFID tags allows for more information to be carried by RFID tag 96 and consequently conveyed to RF interrogator 102. As a result, the administration protocol preprogrammed into RFID tag 96 may contain a substantial amount of detailed and/or sophisticated information. For example, RFID tag 96 typically has the capacity to carry more administration instructions and/or operating parameters for infusion device 14 than some of the previously discussed signaling components.

Figure 16:
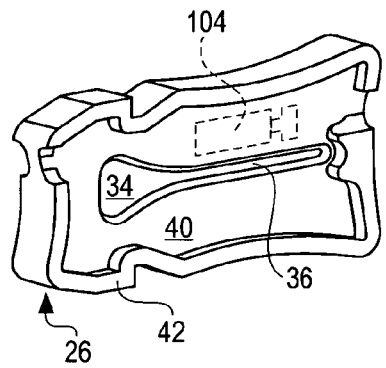
FIG. 16 is a perspective view an ultrasonic signaling component in accordance with an embodiment of the present disclosure.

In another aspect of the present disclosure, the signaling component may be an ultrasonic signaling component 104 as depicted in FIG. 16. Ultrasonic signaling component 104 may have the following properties: a material density, a shape, a geometry and an orientation upon/within slide clamp 26. By varying or altering any of these properties or a combination of these properties, the ultrasonic signaling component may be formed having a distinct ultrasonic detection pattern. Suitable non-limiting materials for ultrasonic signaling component 104 include metal, wood, glass or a polymeric material. Preferred shapes for ultrasonic signaling component 104 include any polygon, a circle or an ellipse. Ultrasonic signaling component 104 may be any object that is capable of providing an ultrasonic detection pattern. Non-limiting examples of suitable ultrasonic signaling components include a small chip or strip of a high density metallic or polymeric material.

The detection device may be an ultrasonic detection device and is preferably an ultrasonic transducer as is commonly known in the art. Ultrasonic transducers typically transmit acoustic energy or sound waves to a target. The sound waves are reflected from the target back to the ultrasonic transducer. The characteristics of the reflected sound waves are based on the properties of the target.

The ultrasonic detection device is preferably adapted to detect the density, the shape, the geometry or the orientation of ultrasonic signaling component 104 disposed on slide clamp 26. The ultrasonic detection device is further preferably configured to identify a distinct administration protocol or a predetermined administration protocol based on the detection pattern of ultrasonic signaling component 104. For example, the ultrasonic detection device may be configured to identify a square-shaped ultrasonic signaling component with a first predetermined administration protocol whereas the ultrasonic detection device may identify an ultrasonic signaling component having a density of 3.7 g/ml with a second predetermined administration protocol.

FIG. 16 shows ultrasonic signaling component 104 disposed within body 40 of slide clamp 26. Ultrasonic signaling component 104 may be placed within body 40 as is commonly known in the art with a driving force or insert molding being preferred. The density or shape of ultrasonic signaling component may be varied in order to provide different ultrasonic detection patterns as previously discussed. FIG. 16 further depicts ultrasonic signaling component 104 longitudinally oriented within slide clamp 26. It is understood that ultrasonic signaling component 104 may be traversely oriented within slide clamp 26 to provide a further varied detection pattern. In addition, the orientation of the ultrasonic signaling component may be varied by altering the location or depth of ultrasonic signaling component 104 within or on slide clamp 26 to provide further differentiation in the ultrasonic signal. Voids in the slide clamp material may provide further differentiation in ultrasonic signals. Ultrasonic signaling component 104 may be disposed within slide clamp 26 as a driven metal pin or as an inserted molded pin, for example.

Figure 17:
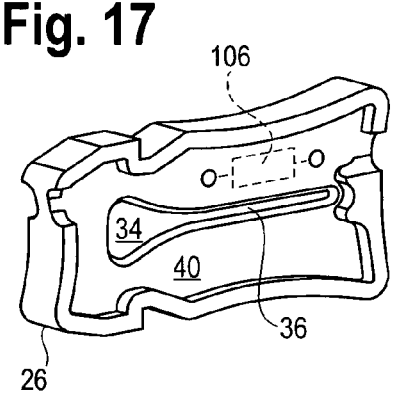
FIG. 17 is a perspective view of an embodiment of the ultrasonic signaling component of FIG. 16.

In an alternate embodiment, an ultrasonic signaling component 106 may be disposed on a surface of slide clamp 26 as shown in FIG. 17. Preferably, ultrasonic signaling component 106 is made of a high density material with metal being preferred. The length, material composition, and orientation of ultrasonic signaling component 106 (i.e., the signaling component longitudinally or traversely disposed relative to the longitudinal axis of the slide clamp) may be varied to provide different ultrasonic detection patterns. Ultrasonic signaling component 106 may be attached to a surface of slide clamp 26 as is commonly known in the art including adhesively affixed, a heat bond, an ultrasonic weld, a press interference fit, or by way of a swaged attachment.

Figure 18:
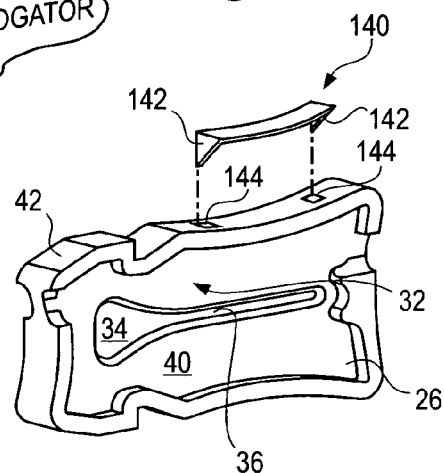
FIG. 18 is an exploded perspective view of a slide clamp having a magnetic signaling component in accordance with the present disclosure.

In another aspect of the present disclosure, the signaling component may be a magnetic signaling component 140 as shown in FIG. 18. A corresponding magnetic detection device (not shown) may be used to detect magnetic signaling component 140 as is commonly known in the art. Magnetic signaling component 140 may be a magnetic material such as a metal-containing material or metal oxide that provides a magnetic detection pattern. The composition, shape, size, geometry or orientation of the magnetic signaling component upon/within slide clamp 26 may be altered, modified or otherwise varied in order to provide differentiation between magnetic detection patterns for the magnetic signaling component detection pattern. In this arrangement, the magnetic detection device detects the magnetic signal in a manner similar to a metal detector. Each distinct magnetic detection pattern may be associated to a corresponding administration protocol as previously discussed.

Alternatively, the magnetic signaling component may be a strip or a piece of magnetic tape having a predetermined magnetic signal corresponding to a desired administration protocol. A specific administration protocol may be associated with or identified by a unique magnetic detection pattern. The magnetic detection device may be configured to detect each different detection pattern and associate or otherwise identify the distinct administration protocol corresponding to each distinct magnetic signaling component to the controller.

Magnetic detection device 140 may be attached to either body 40 or lip 42 of slide clamp 36 as previously discussed. In an embodiment, magnetic signaling component 140 may include legs 142 that may be inserted into holes 144 in lip 42. Once inserted, legs 142 may be swaged in holes 144 to provide permanent attachment between magnetic signaling component 140 and slide clamp 26. Alternatively, magnetic detection device 140 may be disposed within slide clamp 26 as previously discussed.

The present disclosure contemplates that detection device 16 may be a component of infusion device 14 as shown in phantom in FIG. 1. In this arrangement, detection device 16 is preferably located proximate to port 15 and adapted to detect signaling component 38 when slide clamp 26 is secured in port 15. Alternatively, detection device 16 may be a remote detection device located at a location remote from infusion device 14. As a remote detection device, detection device 16 may be operatively connected to infusion device 14 by any suitable connection as is commonly known in the art including non-limiting examples such as an infrared connection, a microwave connection, a radio frequency connection, an electrical connection, a Bluetooth connection, a LAN network connection, a WAN network connection, an Internet connection, a universal serial bus connection and combinations thereof. The remote detection device may be a handheld detection device such as a personal data assistant, for example.

Figure 19:
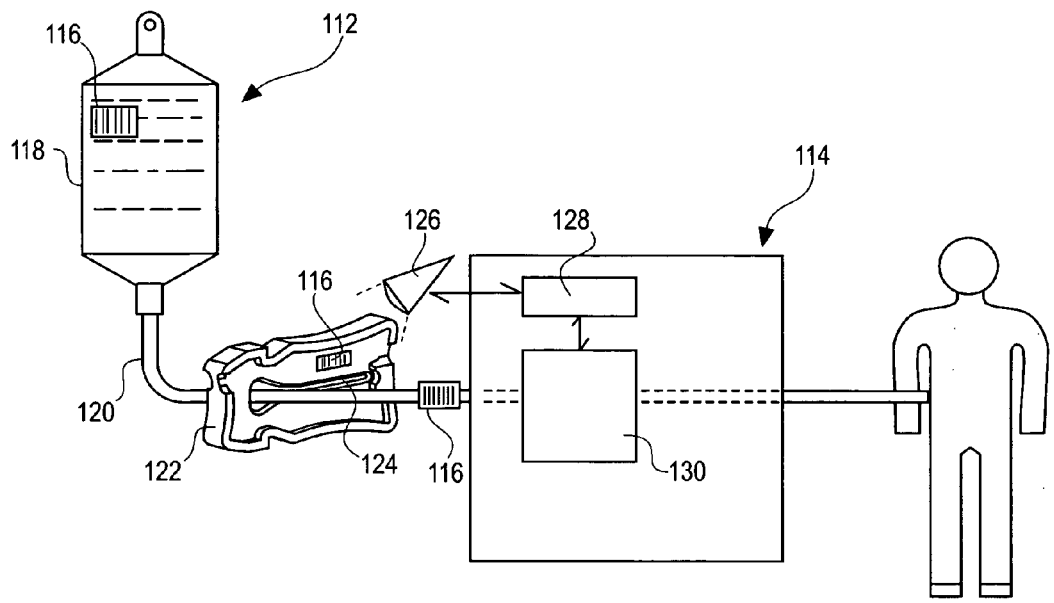
FIG. 19 is a schematic view of an embodiment of the infusion delivery system in accordance with the present disclosure.

In another embodiment of the present disclosure, infusion system 110 includes an infusion set 112, an infusion device 114 and a signaling component 116 as shown in FIG. 19. Infusion set 112 includes an infusate source component 118, an infusate tube component 120 extending from infusate source component 118 and a slide clamp component 122 with an aperture 124 adapted to receive infusate tube component 120.

Signaling component 116 may be disposed on at least one component of infusion set 112. Signaling component 116 contains information indicative of an administration protocol for infusion set 112 as previously described. Infusion device 114 is adapted to detect signaling component 116 and determine the administration protocol indicated by signaling component 116. Infusion device 114 may then be selectively operated or otherwise configured according to the administration protocol detected. Preferably, infusion device 114 is automatically configured to operate according to the administration protocol. It is understood that infusion device 114 may include a control panel or similar user interface that displays the identified administration protocol and enables an operator to manually select or adjust the operating parameters according to the administration protocol.

Signaling component 116 may be disposed on any component of infusion set 112. Thus, signaling component 116 may be disposed on infusate source component 118, infusate tube component 120, or slide clamp component 122 as shown in FIG. 19. It is preferred that signaling component 116 is disposed on a surface of the infusion set component where the infusion set component is infusate source component 118 or infusate tube component 120. Signaling component 116 may include any type of signaling component such as an optical signaling component, an electronic signaling component, a magnetic signaling component, a radio frequency signaling component, and an ultrasonic signaling component as previously discussed.

Infusion device 114 preferably includes a detection device 126 adapted to detect signaling component 116. Detection device 126 may be disposed on an exterior surface of infusion device 114. This enables a health care professional or the infusion patient to place signaling component 116 within the detection zone of detection device 126 regardless of which infusion set component is carrying signaling component 116.

Alternatively, detection device 126 may be a remote and/or a hand-held detection device as previously discussed. It is preferred that the remote/hand-held detection device is sufficiently portable to be moved within the vicinity of any component of infusion set 112 in order to detect a signaling component disposed thereon. Detection device 126 may be operatively connected to a controller 128 or directly to an infusion pump 130 as previously discussed.

Figure 20:
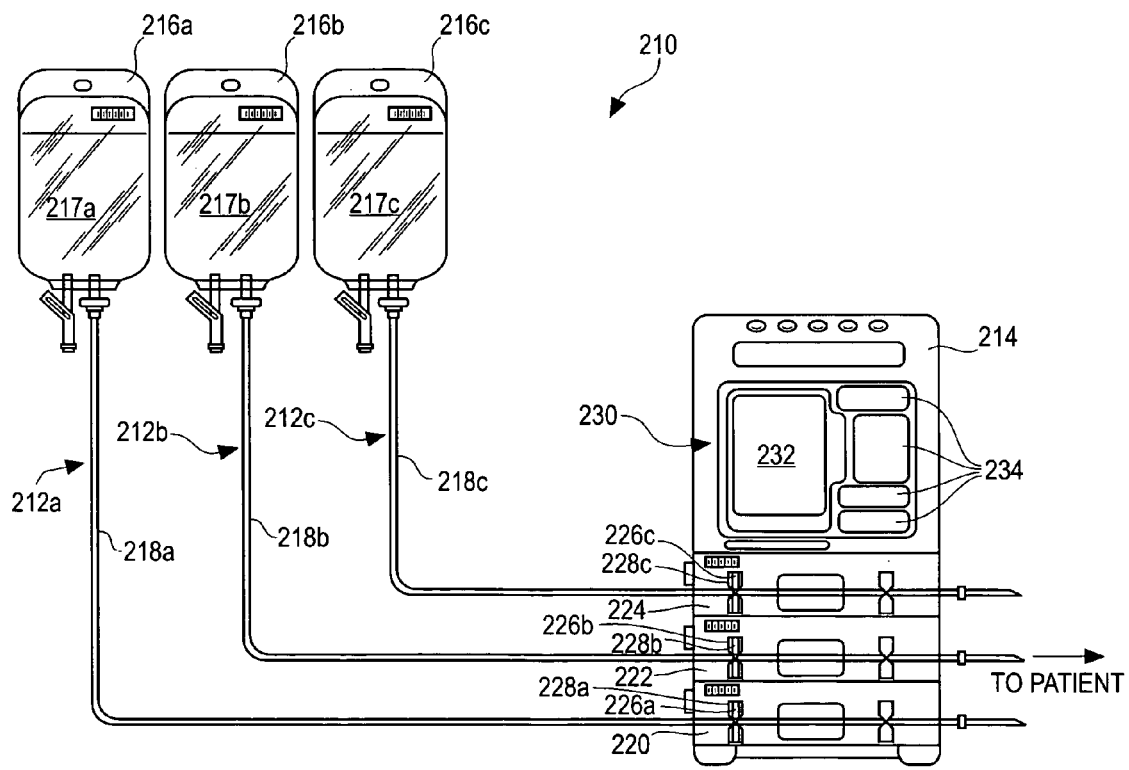
FIG. 20 is a schematic view of an embodiment of the infusion delivery system in accordance with the present disclosure.

In a further embodiment of the present disclosure, infusion system 210 includes a plurality of infusion sets 212a, 212b, 212c and an infusion device 214 as illustrated in FIG. 20. Infusion device 214 may be any type of infusion pump or a syringe pump, for example. In an embodiment, infusion device 214 is an infusion pump that is capable of being programmed and includes a controller that facilitates operation of the pump. Infusion device 214 may further include a memory device capable of storing software therein.

Each infusion set has a corresponding infusate source component 216a, 216b, 216c containing a corresponding infusate 217a, 217b, and 217c. A respective infusate tube component 218a, 218b, and 218c extends from each infusate source component. Infusate tube components 218a-c place infusion device 214 in fluid communication with the contents of each respective infusate source component 216a-c. It is understood that infusion sets 212a-c as well as infusates 217a-c may be the same or different. FIG. 20 depicts infusion system 210 having three infusion sets although an infusion system having as few as one or as many as five or more infusion sets is within the scope of the present disclosure. Infusion device 214 may deliver one or more types of fluids to a patient via a variety of administration protocols. Nonlimiting examples of suitable infusion route types include intravenous, intra-arterial, subcutaneous, epidural, irrigation of fluid spaces, and the like. Non-limiting examples of infusate types that may be delivered by infusion device 214 include parenteral fluids, drugs or other medicaments, electrolytes, blood, blood products and the like.

Infusion device 214 includes three channels 220, 222, and 224, each channel configured to receive a corresponding infusate tube component 218a-c. Channels 220-224 operate to deliver fluid from each infusate source component through each infusate tube component and to the patient. Associated with each infusate tube component is a corresponding slide clamp 226a, 226b, 226c as previously discussed. Each channel includes a respective slide clamp retainer 228a, 228b and 228c that holds or otherwise retains each slide clamp in a respective channel.

Each slide clamp includes a signaling component as previously discussed. In an embodiment, a detection device is located proximate to each slide clamp retainer and is capable of detecting and identifying the administration protocol on the signaling component on each respective slide clamp 226a-c. Thus, the detection device may be a component of infusion device 218. The controller then configures infusion device 214 for operation according to the detected administration protocol.

In an embodiment, infusion device 214 may be configured based on information or data preloaded into the memory storage device. In this situation, the controller receives administration protocol information from the signaling component through the detection device. The controller then compares the detected administration data with the data stored in the memory device. When the detected data matches the stored data, the controller configures the infusion device in accordance with the administration data. Match criteria may be defined in a number of ways. For example, association between certain detected and stored administration parameters may constitute a match. Alternatively, a detected administration protocol value that is within a value range stored in the memory device may also constitute a match. A healthcare facility may customize the controller by defining the preloaded information or the match criteria as desired.

In a further embodiment, infusion device 214 may include a user interface 230 having a display screen 232 and keys 234. Upon configuration of infusion device 214, screen 232 may provide additional graphical or text information regarding some or all of the settings or values of the administration protocol. For example, when infusion device 214 is configured to deliver a certain drug, screen 232 may display governmental or healthcare facility guidelines associated with administration of the drug. System 210 may be configured to operate only after the health care provider has selected a key 234 indicating that these guidelines have been read. The skilled artisan will appreciate that numerous types of information associated with the administration protocol may be displayed on screen 232. User interface 230 may also include an alarm function (either audio, visual, or both) that may escalate if a particular administration event is not addressed by the healthcare professional.

User interface 230 may also be used to adjust some or all of the parameters of the administration protocol used to configure infusion device 214 for operation. Keys 234 may be used to select low level displays and/or adjust operational parameters as is commonly known in the art. Thus, interface 230 enables a user to manually input and/or adjust the administration protocol as well as other operational parameters of system 210.

In an embodiment, the signaling component may be detected either statically or dynamically (i.e., the slide clamp may be detected as it moves past the detection device). For dynamic detection, a timing mark may be disposed on the slide clamp. The timing mark may be detectable by the detection device (or a similar rate detection device) so as to indicate the rate or speed at which the slide clamp is moving with respect to the detection device. Detection of the slide clamp rate of movement (vis-à-vis the timing mark) thereby enables the detection device to properly identify, detect, interpret, or otherwise decode the administration protocol information in the signaling component.

In a further embodiment, the infusion device may include an automated tube loader having a motor. The operation of the tube loader may be coordinated to correspond to the movement rate of the slide clamp (as detected by way of the timing mark). In other words, the rate or speed of the motor used to load the tube may be coordinated with the rate or speed in which the slide clamp moves by the detection device.

EXAMPLES

Two examples of the application of the principles of the present disclosure will now be described.

In the first example, an infusion set having a signaling component on the slide clamp is loaded into the pump. Upon insertion of the slide clamp into the slide clamp retainer on the pump, the detection device of the pump obtains the administration protocol information from the signaling component. In this example, the administration protocol information indicates to the pump that the type of administration associated with the infusion set that was loaded into the pump is enteral. Based on the identification of the enteral administration type, the pump software performs a configuration of the pump for enteral administration based on one of a set of administration profiles associated with enteral administration. In this particular example, the recordation of volume history is enabled by the pump.

In the second example, an infusion set having a slide clamp with a signaling component is loaded into the pump. Upon insertion of the slide clamp into the slide clamp retainer on the pump, the detection device of the pump obtains the administration protocol information from the signaling component. In this example, the administration information indicates to the pump that the type of administration associated with the infusion set that was loaded into the pump is epidural. Based on the identification of the epidural administration type, the pump software performs a configuration of the pump for epidural administration. In this case, the pump initiates a continuous drip of the fluid, disablement of a piggy back feature of the pump, disablement of an air line sensor of the pump, and disablement of an occlusion detection feature of the pump.

It should be understood that various changes and modifications to the presently preferred embodiments described herein will be apparent to those skilled in the art. Such changes and modifications can be made without departing from the spirit and scope of the present disclosure and without diminishing its intended advantages. It is therefore intended that such changes and modifications be covered by the appended claims.

We claim:

1. A slide clamp for use with an infusion device and an infusion set, the infusion set having an infusate source and an infusate tube extending from the infusate source, the slide clamp comprising:
    a body having an aperture adapted to receive the infusate tube; and
    a signaling component configured to communicate information indicative of an administration protocol for the infusion set to a detection device operatively connected to the infusion device, the signaling component including a non-bar code arrangement of curved indentations, wherein each indentation extends only partially into the body of the slide clamp.

2. The slide clamp of claim 1 wherein the slide clamp includes a material selected from the group consisting of polypropylene, polyethylene, acetyl resin, polyester, glycolized polyester, polycarbonate, acrylonitrile butadiene styrene, silica, titanium dioxide, and combinations thereof.

3. The slide clamp of claim 1 wherein the signaling component is selected from the group consisting of an optical signaling component, a mechanical signaling component, and combinations thereof.

4. The slide clamp of claim 3 wherein the signaling component is an optical signaling component selected from the group consisting of, a reflective material, a fluorescent material, a metal component, a color, a translucent material, printing, etching, ink, an ink printed code, ultraviolet pigment, infrared pigment, a heat marking, a laser mark, an arrangement of translucent areas, an indentation disposed on a slide clamp surface, and combinations thereof.

5. The slide clamp of claim 4 wherein the optical signaling component is a laser mark.

6. The slide clamp of claim 5 wherein the slide clamp contains titanium dioxide.

7. The slide clamp of claim 4, wherein the arrangement of indentations is located on a surface of the body.

8. The slide clamp of claim 7 wherein the administration protocol is identified by a characteristic selected from the group consisting of the depth of an indentation, the number of the indentations, the location of the indentations, and combinations thereof.

9. The slide clamp of claim 1 wherein the signaling component is disposed at a location selected from the group consisting of on a surface of the body, within the body, on a lip of the slide clamp, in a lip of the slide clamp, and combinations thereof.

10. The slide clamp of claim 1 wherein the signaling component is affixed to a body surface by an attachment selected from the group consisting of a heat bond, an adhesive material, and a swaged attachment.

11. The system of claim 1 wherein the curved indentations are disposed on the slide clamp in a non-linear array.

12. The slide clamp of claim 1 wherein each of the curved indentations is disposed at one of the corners of the slide clamp.

13. The slide clamp of claim 1 wherein the signaling component is selectively adapted to identify from 1 to about 64 different administration protocols.

14. The slide clamp of claim 1, wherein the administration protocol is identified based upon at least one of (i) a position of the indentations, and (ii) a number of the indentations.

15. A slide clamp for use with an infusion device and an infusion set, the infusion set having an infusate source and an infusate tube extending from the infusate source, the slide clamp comprising:
    a body having an aperture adapted to receive the infusate tube and a substantially flat surface; and
    an optical signaling component configured to communicate information indicative of an administration protocol for the infusion set to a detection device operatively connected to the infusion device, the optical signaling component including a non-bar code arrangement of curved indentations, wherein the arrangement of curved indentations and the substantially flat surface are configured such that light reflected off of the curved indentations allows the detection device to distinguish between that light reflected off of the curved indentations versus light reflected off of the substantially flat surface.

16. A slide clamp for use with an infusion device and an infusion set, the infusion set having an infusate source and an infusate tube extending from the infusate source, the slide clamp comprising:
    a body having an aperture adapted to receive the infusate tube; and
    an optical signaling component configured to communicate information indicative of an administration protocol for the infusion set to a detection device operatively connected to the infusion device, the optical signaling component including a non-bar code arrangement of indentations, wherein each indentation is curved and extends only partially into the body of the slide clamp.

17. The slide clamp of claim 15, wherein the substantially flat surface has a lighter color than the color of each indentation.

* * * * *

UNITED STATES PATENT AND TRADEMARK OFFICE
CERTIFICATE OF CORRECTION

| | | |
|---|---|---|
| PATENT NO. | : 8,679,075 B2 | Page 1 of 1 |
| APPLICATION NO. | : 11/345512 | |
| DATED | : March 25, 2014 | |
| INVENTOR(S) | : Lurvey et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1714 days.

Signed and Sealed this
Twenty-first Day of July, 2015

Michelle K. Lee
*Director of the United States Patent and Trademark Office*